United States Patent [19]

Hardtmann et al.

[11] 3,983,242

[45] Sept. 28, 1976

[54] 3-ALKYLSULFINYL-2-INDOLINONES AND THEIR PHARMACEUTICAL COMPOSITIONS AND USE

[75] Inventors: Goetz E. Hardtmann, Morristown; Thomas E. Jackson, Madison, both of N.J.

[73] Assignee: Sandoz, Inc., E. Hanover, N.J.

[22] Filed: Sept. 8, 1975

[21] Appl. No.: 611,174

[52] U.S. Cl. .............................. 424/274; 260/325 R
[51] Int. Cl.$^2$ ................ A61K 31/40; C07D 209/34
[58] Field of Search.................. 260/325 R; 424/274

[56] References Cited
UNITED STATES PATENTS
3,882,236   5/1975   Molloy................................. 424/274

OTHER PUBLICATIONS
Gassman, "J.A.C.S.," vol. 96, pp. 5508–5517 (1974).

Primary Examiner—Lewis Gotts
Assistant Examiner—S. P. Williams
Attorney, Agent, or Firm—Gerald D. Sharkin; Richard E. Vila; Frederick H. Weinfeldt

[57] ABSTRACT

3-Alkylsulfinyl-2-indolinones, of the formula

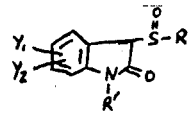

e.g., 3-methylsulfinyl-5-trifluoromethyl-2-indolinone, are useful as minor tranquillizers, muscle relaxants and sedative-hypnotics and are obtainable by oxidizing corresponding 3-alkylthio-2-indolinones.

12 Claims, No Drawings

3-ALKYLSULFINYL-2-INDOLINONES AND THEIR PHARMACEUTICAL COMPOSITIONS AND USE

This invention relates to organic compounds and more particularly to 3-alkylsulfinyl-2-indolinones and their non-toxic pharmaceutically acceptable salts, as well as to pharmaceutical compositions containing such compounds and the use of such compounds.

The compounds of this invention may be conveniently represented by the formula I:

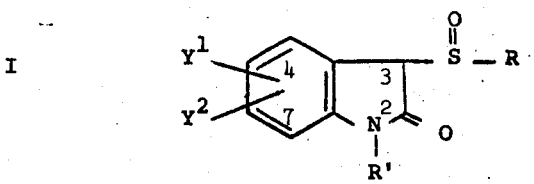

wherein
R is alkyl having from 1 to 4 carbon atoms, preferably methyl;
R' is a hydrogen atom or alkyl having from 1 to 4 carbon atoms;
$Y^1$ is a hydrogen atom, halo having an atomic weight of from about 19 to 80, i.e., fluoro, chloro or bromo, alkyl having from 1 to 3 carbon atoms, alkoxy having from 1 to 3 carbon atoms; or trifluoromethyl; and
$Y^2$ is a hydrogen atom, halo having an atomic weight of from about 19 to 80 or alkyl having from 1 to 3 carbon atoms.

Compounds I are obtainable by oxidizing (process a) a corresponding thioalkyl compound, i.e., a compound of formula II:

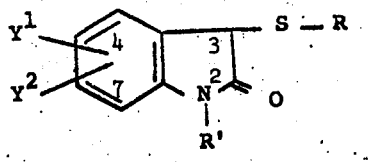

wherein R, R', $Y^1$ and $Y^2$ are as defined above, i.e., by introducing an oxygen atom at the sulfur atom of the thioalkyl function of a compound II.

Process (a) may be carried out in a conventional manner for oxidizing a thioalkyl function to a sulfinyl function. For example, Process (a) may be conveniently carried out by reacting a compound II, (as defined above), with an oxidizing agent in an inert organic solvent, at a moderate temperature, e.g., at from about 0° to 50°C., preferably at from about 0° to 15°C. Suitable oxidizing agents include organic peracids, such as m-chloroperbenzoic acid and peracetic acid, and inorganic peroxides, such as sodium meta-periodate or hydrogen peroxide. In addition, positive heavy halogen oxidizing agents may be used, such as $Br_2$, $Cl_2$, N-bromosuccinamide or iodobenzenedichloride. m-Chloroperbenzoic acid, however, is preferred (also known as meta-chloroperoxybenzoic acid). Suitable solvents are chlorinated lower hydrocarbons, e.g., methylene chloride, lower alkanols, e.g., methanol, and ethers, e.g., dioxane or tetrahydrofuran, preferably methylene chloride. Although in theory only a stoiciometeric equivalent of the oxidizing agent is required for the reaction, a small excess may be included, e.g., of from about 0.05 to 0.5 equivalents excess, where such appears advantageous.

The products of the above-described reaction may be recovered and refined in conventional manner, e.g., by crystallization, distillation or chromatographic techniques, such as eluting from a chromotographic column or separating on a silica layer.

Some of the above-defined compounds II are known and are obtainable by means described in the literature, e.g., J.A.C.S. 96, 5508–5517 (1974), while those not known may be prepared by methods analogous to those described in the literature for the preparation of the known compounds.

Preferred compounds I are those in which R is methyl, and those in which there is a substituent at the 5-position, particularly a trifluoromethyl group. It is also generally preferred that R' is hydrogen or alkyl of 1 to 2 carbon atoms.

STATEMENT OF UTILITY

The compounds of formula I are useful because they possess pharmacological activity in animals. In particular, the compounds are minor tranquilizers useful in the treatment of anxiety as indicated (1) by docility in behavior tests in mice given from about 10 to 200 mg. per kilogram of animal body weight, i.p. of the test compound according to the 30-word adjective check sheet system basically as described by Irwin, S. (Gordon Research Conference, Medicinal Chemistry (1959) and Chen (Symposium on Sedative and Hypnotic Drugs, Williams and Wilkins, 1954); (2) by a reduction of hexobarbital anesthesia in mice (10 to 200 mg./kg.); (3) by an indication of chemically induced seizures in mice on intraperitoneal administration (10–200 mg./kg.) using 50 mg./kg. of N-sulfamoylazepine to induce seizures; and (4) by a potentiation of Thioridazine as determined by a loss of righting reflex according to the method of Reed-Muench, Am. J. Hygiene, 27: 493–497 (1937), in which fastened but glucose maintained mice are administered 12.5 mg./kg. i.p. of Thioridazine followed immediately by the administration of graded doses totally from 10 to 150 mg./kg., i.p. of the test compound in a volume 0.1 ml./kg., of body weight, the mice being scored for loss of righting reflex sixty minutes after dosing.

The compounds I are also muscle relaxants useful in relieving muscle tension as indicated by the above docility test and by a neurological deficit and muscle relaxation in the "rotarod test" in mice on administration intraperitoneally (10–200 mg./kg.) essentially according to the method of Dunham et al., J. Am. Pharm. Assoc. 45:208, 1957.

The compounds I are further useful as sedatives having a hypnotic effective as indicated by the above-indicated Thioridazine test and by a reinduction of hexobarbital anesthesia in mice (10–200 mg./kg.)

For such usage, the compounds may be administered orally or parenterally, preferably orally, and in admixture with conventional pharmaceutical carriers. The dosage administered may vary depending upon known variables such as the particular compound employed and the severity of the condition being treated. In general, satisfactory results are obtained for use as minor tranquilizers and muscle relaxants when administered at a daily dosage of about 2 milligrams to about 150 milligrams per kilogram of animal body weight, preferably given orally and in divided doses, 2 to 4 times a day, or in sustained release form. For large animals, the total daily dose is from about 120 milligrams to about 1,500 milligrams of the compound, and the dosage forms suitable for internal administration comprise from about 30–800 mg of the compound in admixture with the solid or sterile liquid, pharmaceutically-acceptable carrier or diluent. In general, satisfactory results for use of compounds I as sedative hypnotics are obtained when administered at a bedtime dosage of from about 2 milligrams to about 150 milligrams per kilogram of animal bodyweight, preferably given orally. For large mammals, the total dose is from about 120 milligrams to about 1000 milligrams h.s. of the compound, and the dosage forms suitable for internal administration comprise from about 60 to 500 mg of the compound in admixture with the solid or sterile liquid, pharmaceutically-acceptable carrier or diluent.

For the above uses, compounds I may be administered orally in such forms as tablets, dispersible powders, granules, capsules, syrups and elixirs; and parenterally as solutions, suspensions, dispersions, emulsions, and the like, e.g., a sterile injectable formulation such as an aqueous suspension. These pharmaceutical compositions may contain from about 0.5% up to about 90% of the active ingredient in combination with the carrier or adjuvant, more usually between 10% and 80% by weight. Such compositions may be prepared according to any method known in the art for the manufacture of pharmaceutical compositions, and such compositions may contain one or more conventional adjuvants, such as sweetening agents, flavoring agents, coloring agents and preserving agents, in order to provide an elegant and palatable preparation.

The preferred pharmaceutical compositions from the standpoint of preparation and ease of administration are solid orally administrable compositions, particularly tablets and solid or liquid diluent-filled capsules (as appropriate to the nature of the particular active ingredient), containing for example from about 30 to 1000 mg. of the active ingredient.

Compounds I are relatively acidic and will form salts with bases. Such salt form may be conveniently represented by the formula Iq:

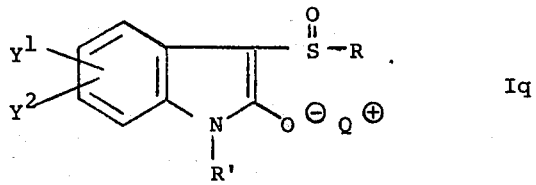

wherein $Y^1$, $Y^2$, R and R' are as defined above and $Q^{\oplus}$ is a cation. The pharmaceutically acceptable salts thereof are included within the scope of the pharmaceutically useful compounds of the present invention. Such salts are the pharmaceutical equivalents of their free forms, and include, by way of illustration, the sodium salt and the triethyl ammonium salt. In general, the salts may be produced from the free forms (acidic) by established procedures. Conversely, the free compounds may be obtained from their salts by the well-known procedures. It will be appreciated that while the compounds I are generally referred to in the processes herein described as in free form, they may actually be present in the form of their corresponding salts under particular reaction conditions, and may be recovered directly in pharmaceutically acceptable salt form by conventional methods.

Tablets and capsules containing the ingredients indicated below may be prepared by conventional techniques and are useful as muscle relaxants and in treating tension and anxiety at a dose of one tablet or capsule 2 to 4 times a day, or as sedative-hypnotics at a dose of, e.g., 2 to 4 tablets or capsules h.s.:

| Ingredient | Weight in Milligrams | |
|---|---|---|
| | Tablet | Capsule |
| 3-methylsulfinyl-5-trifluoro-methyl-2-indolinone | 100 | 100 |
| Tragacanth | 10 | — |
| Lactose | 147.5 | 120 |
| Corn Starch | 25 | — |
| Talcum | 15 | — |
| Magnesium Stearate | 2.5 | — |

In the following examples, which are illustrative of the invention, temperatures are in degrees centigrade, and room temperature is 20° to 30°C, unless indicated otherwise.

EXAMPLE 1

3-Methylsulfinyl-5-trifluoromethyl-2-indolinone

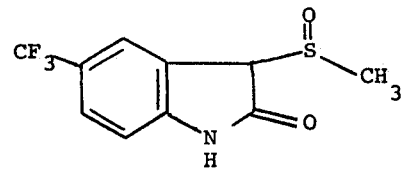

STEP A: Preparation of 3-methylthio-5-trifluoromethyl-2-indolinone

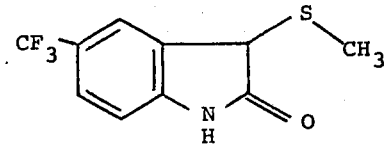

To a solution of 30.8 of p-aminobenzotrifluoride predissolved in 450 ml. of methylene chloride, cooled to −58°C. (dry ice/isopropanol bath), and under an atmosphere of nitrogen, is added dropwise a solution of 21.1 ml. of t-butyl hypochlorite in 30 ml. of methylene chloride over 30 minutes while the reaction miture is maintained at −55° to 58°C. After the reaction mixture is stirred an additional five minutes, a solution of 25.6 g. of ethyl methylthioacetate in 30 ml. of methylene chloride is added dropwise over a period of 20 minutes while the reaction mixture is maintained at −55° to −58°C. The reaction mixture is stirred one hour at −55° to −65°C. and 60 ml. of methylene chloride is added to facilitate stirring. A solution of 25 ml. of triethylamine in 25 ml. of methylene chloride is added dropwise over a period of 10 minutes while the reaction mixture is maintained at −50°C. to −60°C. After an additional three minutes stirring, the cold bath is removed and the reaction mixture allowed to warm to 15°C. over a period of two hours; then 100 ml. of water is added. The organic phase is separated and concentrated in vacuo to an oil which is then dissolved in 100 ml. of ether. The ethereal solution is treated with 50 ml. of 2N hydrochloric acid, and the mixture is stirred overnight at room temperature. The phases are separated and the product is obtained in two portions by crystallization with cooling, followed by concentration of the mother liquors to a solid in vacuo. Recrystallization from ether/pentane gives 3-methylthio-5-trifluoromethyl-2-indolinone, m.p. 136°–138°C.

STEP B: Preparation of
3-methylsulfinyl-5-trifluoromethyl-2-indolinone

To a cooled (ice/water) solution of 9.4 g. of 3-methylthio-5-trifluoromethyl-2-indolinone predissolved in 318 ml. of methylene chloride is added 7.33 g. of m-chloroperoxybenzoic acid in small portions over a period of one minute. The ice/water bath is then removed; and, after eight minutes stirring, the reaction mixture is filtered (after the peracid is dissolved and before the product precipitates). The reaction mixture is stirred for an additional hour during which product precipitates. The product is then collected by filtration. Recrystallization from ethyl acetate/ligroine gives 3-methylsulfinyl-5-trifluoromethyl-2-indolinone, m.p. 141°–142°C.

EXAMPLE 2

Repeating the procedure of Step B of Example 1 but replacing the 3-methylthio-5-trifluoromethyl-2-indolinone used therein with an approximately equivalent amount of
a. 3-methylthio-2-indolinone;
b. 3-ethylthio-5-trifluoromethyl-2-indolinone;
c. 1-ethyl-3-methylthio-5-trifluoromethyl-2
d. 5-chloro-3-methylthio-2-indolinone;
e. 5-methyoxy-3-methylthio-2-indolinone
f. 5-methyl-3-methylthio-2-indolinone;
g. 4,6-dichloro-3-methylthio-2-indolinone; or
h. 7-chloro-3-methylthio-4-trifluoromethyl-2-indolinone;
there is similarly obtained:
a. 3-methylsulfinyl-2-indolinone;
b. 3-ethylsulfinyl-5-trifluoromethyl-2-indolinone;
c. 1-ethyl-3-methylsulfinyl-5-trifluoromethyl-2-indolinone;
d. 5-chloro-3-methylsulfinyl-2-indolinone;
e. 5-methoxy-3-methylsulfinyl-2-indolinone;
f. 5-methyl-3-methylsulfinyl-2-indolinone;
g. 4,6-dichloro-3-methylsulfinyl-2-indolinone; and
h. 7-chloro-3-methylsulfinyl-4-trifluoromethyl-2-indolinone.

What is claimed is:
1. A compound which is an indolinone of the formula:

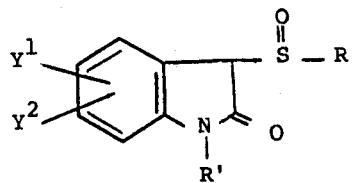

wherein
R is alkyl having from 1 to 4 carbon atoms,
R' is a hydrogen atom or alkyl having from 1 to 4 carbon atoms,
$Y^1$ is a hydrogen atom, trifluoromethyl, halo having an atomic weight of from about 19 to 80, alkyl having from 1 to 3 carbon atoms, or alkoxy having from 1 to 3 carbon atoms; and
$Y^2$ is a hydrogen atom, halo having an atomic weight of from about 19 to 80 or alkyl having from 1 to 3 carbon atoms; or a
non-toxic pharmaceutically acceptable salt thereof.
2. A compound of claim 1 in which R' is a hydrogen atom.
3. A compound of claim 2 in which $Y^1$ is at the 5-position and is other than a hydrogen atom.
4. A compound of claim 5 in which $Y^1$ is trifluoromethyl.
5. The compound of claim 4 which is 3-methylsulfinyl-5-trifluoromethyl-2-indolinone.
6. A compound of claim 1 in which R' is alkyl.
7. A compound of claim 6 in which $Y^1$ is at the 5-position and is other than a hydrogen atom.
8. A compound of claim 7 in which $Y^1$ is trifluoromethyl.
9. A pharmaceutical composition which is useful in sedating or relieving anxiety or muscular tension in a mammal comprising an effective amount of a compound of claim 1 and a pharmaceutically acceptable carrier.
10. A method of treating anxiety in a mammal in need of such treatment which comprises internally administering an amount of a compound of claim 1 effective in relieving anxiety in said mammal.
11. A method of treating muscular tension in a mammal in need of such treatment which comprises internally administering an amount of a compound of claim 1 effective in relieving muscular tension in said mammal.
12. A method of sedating a mammal in need of such treatment which comprises internally administering an amount of a compound of claim 1 effective in inducing a sedative-hypnotic effect in said mammal.

* * * * *